United States Patent [19]

Dennis

[11] Patent Number: 4,857,315
[45] Date of Patent: Aug. 15, 1989

[54] COMPOSITIONS CONTAINING GOLGI ALPHA-MANNOSIDASE II INHIBITORS

[75] Inventor: James W. Dennis, Etobicoke, Canada

[73] Assignee: Mount Sinai Hospital Corporation, Toronto, Canada

[21] Appl. No.: 65,248

[22] Filed: Jun. 18, 1987

Related U.S. Application Data

[63] Continuation-in-part of Ser. No. 912,485, Sep. 29, 1986, abandoned, and a continuation-in-part of Ser. No. 912,486, Sep. 29, 1986, abandoned.

[51] Int. Cl.$^4$ .................... A61K 45/02; A61K 31/70
[52] U.S. Cl. ................................ 424/85.2; 424/85.6; 424/85.7; 514/44
[58] Field of Search ..................... 424/85, 195.1, 85.2, 424/85.6, 85.7; 514/44, 299; 546/183, 112

[56] References Cited

FOREIGN PATENT DOCUMENTS 0104826 4/1984 European Pat. Off. .

OTHER PUBLICATIONS

Humphries et al., Proc. Natl. Acad. Sci., vol. 83, pp. 1752–1756, Mar. 1986.
Goldstein et al., Cancer Research, vol. 46, pp. 4315–4329, 1986.
Chemical Abstracts, vol. 101, Abstract No. 28283x, 1984.
Chemical Abstracts, vol. 103, Abstract No. 81429s, 1985.
Nicolson, G. L., Biochem. Biophys. Acta. 695:113, 1982.
Poste, G. and Fidler, I. J., Nature 283:139, 1980.
Weiss, L., Semin. Oncl. 4:5–19, 1977.
Dennis, J. W. et al., Nature 292:242, 1981.
"Asparagine-Linked Oligosaccharides in Murine Tumor Cells: Comparison of a WGA-Resistant Nonmetastatic Mutant and a Related WGA-Sensitive Metastatic Line", Dennis, J. W. et al., J. Cell Biol. 99:1034, 1984.
"Partial Reversion of the Metastatic Phenotypes in a WGA Resistant Mutant of MDAY-D2 Selected with Bandeiraea Simplicifolia Seed Lectin BSII", Dennis, J. W., J. Natl. Cancer Inst. 74:1111, 1985.
Takasai, S. et al., Biochem. Biophys. Res. Commun. 92:735–742, 1980.
Yogeswarren, G., and Salk, P. L., Science (Wash. D.C.), 1514–1516, 1981.
Finne, J. et al., Cancer Res., 40:2580–2587, 1980.
Dennis et al., J. Cell. Biol. 99:1034–1044, 1984.
Yamashita K. et al., J. Biol. Chem. 259, 10834, 1984.
"Studies of an Immunomodulator, Swainsonine, I. Enhancement of Immune Response by Swainsonine In Vitro", Motohiro, Hino, et al., J. Antibiotics. 926–940, Jul. 1985.
Crisuodo, B. A., and Krag, S. S., J. Cell Biol. 94:586–591, 1982.
Zullo, Z. N. et al., Cell 43:783, 1985.
Lin, S. L. et al., Science 233:356–358, 1986.
Morin, M. J. et al., Can. Res. 43:1669–1674, 1983.
Einat, M. et al., Nature 313, 597, 1985.
Lau, L. F., and Nathans, D., Proc. Natl. Acad. Sci. U.S.A., 84, 1182, 1987.
Whitfield, J. F. et al., Cancer and Metastasis Reviews, 5, 205, 1987.
Goldstein, D., and Lasglo, J., Can. Res. 64:4315, 1986.
Levine, A. S. et al., Can. Res. 39:1645–1650, 1970.
Hunter, T., Nature 322:14–16, 1986.
Moheshwari, R. K. et al., Science 219:1339–1341, 1983.
Tulsiani, D. R. P. et al., J. Biol. Chem. 258:7578, 1983.
Pierce M. and Arango J., J. Biol. Chem. 261, 10772, 1986.

(List continued on next page.)

*Primary Examiner*—Blondel Hazel
*Attorney, Agent, or Firm*—Rogers, Bereskin & Parr

[57] ABSTRACT

The invention relates to compositions containing an inhibitor of the Golgi enzyme α-mannosidase II and which may contain an interferon or interferon inducer and to methods of preventing and treating diseases, such as proliferative diseases, viral infections and neoplastic growth and metastasis with the compositions.

18 Claims, 7 Drawing Sheets

OTHER PUBLICATIONS

Debray H. et al., Int. J. Cancer 37, 607, 1986.
Dennis, J. W. et al., Science, 236:582, 1987.
Kerbel, R. S. et al., Proc. Natl Acad. Sci., U.S.A., 84, 1263, 1987.
Molyneux, R. J. and James, L. F., Science (Wash. D.C.) 216:190–191, 1981.
"Swainsonine Inhibits the Biosynthesis of Complex Glycoproteins by Inhibition of Golgi Mannosidase II", Tulsiani, D. R. P. et al., J. Biol. Chem. 257:7936–7939, 1982.
Tulsiani, D. R. P. and Touster, O., J. Biol. Chem. 260:13081–13087, 1985.
"The Similar Effects of Swainsonine and Locoweed on Tissue Alycosidases and Oligosaccharides of the Pig Indicate that the Alkaloid is the Principal Toxin Responsible for the Induction of Locoism", Tulsiani, D. R. P., et al., Arch. Biochem. Biophys., 232:76–85, 1984.
"Oligosaccharide Modification by Swainsonine Treatment Inhibits Pulmonary Colonization by B16-F10 Murine Melanoma Cells", Humphries, M. J. et al., Proc. Natl. Acad. Sci, U.S.A., 83:1752–2756, 1986.
Keller, R. K. et al., Biochem. 18:3946–3952, 1979.
Irimura et al., Cancer Res. 41:3411–3418, 1981.
Gibson, R. et al., Trends in Biochem. Sci. Nov. 290–293, 1980.

COMPOSITIONS CONTAINING GOLGI ALPHA-MANNOSIDASE II INHIBITORS

This application is a continuation-in-part of my applications for U.S. patent Ser. Nos. 912,485 now abandoned and 912,486 now abandoned, both filed on Sept. 29, 1986, which are incorporated herein by reference.

BACKGROUND OF THE INVENTION

The invention relates to compositions and to methods of preventing and treating diseases such as proliferative disorders, viral infections and neoplastic growth and metastasis with the compositions.

Continuous proliferation of tumor cells is a primary requirement for malignancy. It has been disclosed that most cancers are ultimately lethal because of their ability to metastasize and form tumors at secondary sites (Nicolson, G. L., Biochem. Biophys. Acta. 695: 113, 1982; Poste, G. and Fidler, I. J. Nature 283: 139, 1980; and Weiss, L., Semin. Oncl. 4: 5-19, 1977). Therefore, there is a need for drugs or biological response modifiers capable of inhibiting both metastasis as well as tumor cell proliferation. In this regard, it has been disclosed that certain glycoconjugate structures found on the tumor cell surface contribute directly to the manifestation of the metastatic phenotype. (Nicolson, G. L., Biochem. Biophys. Acta (695: 113, 1982).

Previous work done by the inventor and others has indicated that modification of Asn-linked carbohydrates on malignant cells reduces metastatic potential. (Dennis, J. W. et al Nature 292: 242, 1981; Dennis, J. W. et al. J. Cell Biol. 99: 1034, 1984; Dennis, J. W. J. Natl. Cancer Inst. 74: 1111, 1985; Takasai, S., et al, Biochem. Biophys. Res. Commun. 92: 7365-742, 1980). For a number of murine tumor cell lines it has been shown that sialylation of available cell surface galactose and N-acetylgalactosamine enhances metastatic potential. (Yogeswarren, G., and Salk, P. L., Science (Washington DC), 1514–1516, 1981). It has also been shown that loss of sialylated Asn-linked oligosaccharides in lectin resistant mutants of the B16 melanoma and the MDAY-D2 tumor cell lines decreases metastatic potential (Finne, J. et al. Cancer Res., 40: 2580-2587, 1980; Dennis et al, J. Cell. Biol. 99: 1034-1044, 1984.). In addition, the inventor has shown that loss of these structures reduces the growth rate of the tumor cells in situ. (Kerbel, R. S., Dennis, J. W. et al, Cancer Mestastasis Reviews 1, 99, 1982).

Malignant transformation of murine and human cells often leads to increased branching of Asn-linked oligosaccharides (Yamashita K. et al., J. Biol. Chem. 259, 10834, 1984; Pierce M. and Arango J., J. Biol. Chem. 261, 10772, 1986; Debray H. et al., Int. J. Cancer 37, 607, 1986) and this in turn may increase the sialic acid levels in the glycoconjugates. Recent work done by the inventor has shown that increased branching is not directly related to the transformed phenotype but can occur subsequently as a result of a secondary change in gene expression. Most importantly, increased branching of Asn-linked oligosaccharides was shown by the inventor to be directly related to metastatic potential of the tumor cells (Dennis J. W. et al., Science, 1987), and may also endow the tumor cells with a selection growth advantage in vivo. (Kerbel R. S. et al, Proc. Natl Acad. Sci. U.S.A., 84, 1263, 1987).

Swainsonine (SW) is found in spotted locoweed and when ingested by domestic farm animals, the compound inhibits lysosomal mannosidase as well as Golgi α-mannosidase II (Molyneux, R. J. and James, L. F., Science (Washington DC) 216: 190–191, 1981; Tulisani, D. R. P. et al. J. Biol. Chem. 257: 7936–7939, 1982). The brain tissues accumulate lysosomal vesicles containing oligomannose structures similar to that observed in hereditary lysosomal storage diseases. There are a number of tissue-specific mannosidases, and it has been found that rodents have a brain enzyme that is not inhibited by swainsonine (Tulsiani, D. R. P. and Touster, O., J. Biol. Chem. 260: 13081–13087, 1985). In addition, it has been found that rat brain does not accumulate oligomannose structures and the animals do not show neurological symptoms when fed the compound. (Tulsiani, D. R. P. et al. Arch. Biochem Biophys. 232: 76–85, 1984). Most significantly, it has been found that Swainsonine blocks branching of Asn-linked oligossacharides by competatively inhibiting the golgi processing enzyme α-mannosidase II (Tulsioni, D. R. P., J. Biol Chem 258, 7578, 1983).

Humphries et al. (Proc. Natl. Acad. Sci. USA 83: 1752–2756, 1986), have found that treatment of B16F10 murine melanoma cells with swainsonine inhibits their ability to colonize the lungs of C57BL/6 mice after intravenous injection of the B16F10 cells. However, the treatment was found to have no effect on B16F10 viability or on tumorigenicity after subcutaneous implantation. In the study swainsonine was not administered to tumor-bearing mice.

Tunicamycin, is an antibiotic produced by *Streptomyces lysosuperficus*, and it has been found to inhibit the first step in the formation of Asn-linked oligosaccharide chains (Keeler, R. K. et al., Biochem. 18: 3946–3952, 1979). It has been shown that B16 melanoma cells grown overnight in tunicamycin are less efficient at lung colonization (Irimura et al., Cancer Res. 41, 3411–3418, 1981). However, tunicamycin causes gross disfunction of glycoprotein localization and function in the cell (Gibson R. et al., Trends in Biochem. Sci. Nov. 290–293, 1980) and thus has been found to be toxic for many cell types (Crisuodo, B. A. and S. S. Krag, J. Cell Biol. 94: 586–591, 1982).

Interferons are proteins secreted by animal cells in response to viruses as well as growth factors (Zullo, Z. N., et al., Cell 43: 793, 1985). Interferon binds to a cell surface receptor and manifests a number of biological responses including antiviral effects and inhibition of cell growth (S. L. Lin et al., Science 233: 356–358, 1986).

Interferon has been shown to reduce the expression of the c-myc oncogene in human cell lines (Einat M. et al., Nature 313, 597, 1985), c-myc is one of the cellular genes that is actively transcribed in cells stimulated to proliferate (Lau L. F. and Nathans D., Proc. Natl. Acad. Sci. USA 84, 1182, 1987) and is through to be required for cell proliferation (Whitfield J. F. et al., Cancer and Metastasis Reviews 5, 205, 1987). As such, the level of c-myc mRNA in cells can be used as an indicator of the cells growth state.

Interferons have been used in clinical trials for the treatment of most types of cancer (Goldstein, D., and Lasglo, J., Can. Res. 46: 4315, 1986). Significant response rates to interferons have been observed with hairy cell leukemia and lymphomas, while other tumor types have been found to be less responsive. High concentrations of interferon are often required and this has life threatening side effects, for example, hypotension and renal failure (Levine A. S. et al., Can. res. 39: 1645-1650, 1979).

A number of inducers of interferon have been disclosed. Polyinocinic, polycytidylic acid (Poly (I.C.)), a synthetic double-standed RNA is an effective inducer of interferon in vitro and in vivo. Poly (I.C.)-lysine (poly (I.C.).LC) is more stable in humans than poly (I.C.) and it has been used in clinical studies (Levine, A. S. et al., Cancer Res. 39: 1645-1650). T. Hunter (Nature 322: 14-16, 1986) has reviewed other inducers of interferon, namely transforming growth factor (TGF-$\beta$) and tumor necrosis factor (TNF).

It has been found that tunicamycin enhances the antiviral effects of interferon on enveloped viruses and enhances the antiproliferative effect of interferon on 3T3 fibroblasts (Moheshwari, R. K. et al., Science 219: 1339-1341, 1983). Tunicamycin has not been used clinically due to its toxicity (Morin, M. J. et al., Can. Res. 43: 1669-1674, 1983).

SUMMARY OF THE INVENTION

Broadly stated the invention provides a composition comprising an inhibitor of Golgi $\alpha$-mannosidase II and which may contain an interferon or interferon inducer. The composition comprising an inhibitor of Golgi $\alpha$-mannosidase II, in pharmaceutical formulation, inhibits cancer metastasis and cell proliferation. The composition, hereinafter referred to as the enhancing composition, comprising an inhibitor of the Golgi enzyme $\alpha$-mannosidase II and an interferon or interferon inducer enhances the antiproliferative and antiviral effects of interferons or interferon inducers, and inhibits neoplastic growth and metastasis.

The invention broadly contemplates a method for the prevention and treatment of proliferative disorders and cancer metastasis comprising administering to a patient an effective amount of an inhibitor of Golgi $\alpha$-mannosidase II and a pharmaceutically acceptable carrier. The invention also broadly contemplates a method for the prevention and treatment of proliferative disorders, viral infections, and neoplastic growth and metastasis comprising administering to a patient an effective amount of an inhibitor of the Golgi enzyme $\alpha$-mannosidase II and an effective amount of an interferon or interferon inducer.

A previous study has shown that treatment of B16F10 murine melanoma cells with swainsonine inhibits their ability to colonize the lungs of C57BL/6 mice. (Humphries et al. Proc. Natl. Acad. Sci. OSA: 83, 1752-2756, 1986). However, hitherto, swainsonine has not been administered to tumor-bearing animals nor has it been previously suggested that swainsonine could be used as a therapeutic agent for prevention and treatment of cancer metastasis.

In accordance with the present invention, metastasis has been reduced after administration of swainsonine alone. The swainsonine was orally administered into groups of mice who were subsequently injected intravenously with swainsonine treated B16F10 melanoma cells. The mice were shown to have significantly fewer lung modules than control mice injected with untreated and swainsonine treated B16F10 melanoma cells. Similar results were obtained using the murine lymphoreticular tumor line MDAY-D2 and the human colon carcinoma cells.

Swainsonine alone administered in the drinking water of nude mice reduced the growth rate of a human colon carcinoma cell line subsequently transplanted into the mice. Similarly, the doubling time of human carcinoma cells in vitro was increased by the addition of swainsonine to the culture medium. HT29m human colon carcinoma cells cultured in the presence of swainsonine showed decreased c-myc expression as expected for cells in a lower proliferative state.

The enhancing composition according to the invention is superior to interferon or interferon inducers alone for the treatment and prevention of proliferative diseases, viral infections and neoplastic growth and metastasis since it allows smaller doses of interferon and interferon inducers to be administered and reduces toxicological problems.

Significant inhibition of solid tumor growth was observed when swainsonine in combination with the interferon-inducer poly (I.C.) was administered to mice injected with the lymphoreticular tumor cell line MDAY-D2. It is unexpected that the action of swainsonine and the interferon-inducer poly (I.C.) is not additive, but on the contrary is synergistic. Swainsonine was also found to enhance the antiproliferative effect of mouse $\alpha/\beta$ interferon on MDAY-D2 tumor cells in vitro, indicating that the inhibitory effect of swainsonine and interferons is due to inhibition of tumor cell proliferation.

Metastasis was also reduced after administration of swainsonine and poly (I.C.) into groups of mice injected with B16F10 tumor cells.

Oral administration of swainsonine in combination with systemic administration of human $\alpha_2$-interferon synergized to inhibit HT29m human colon carcinoma cell growth in nude mice. Swainsonine also enhanced the antiproliferative effects of interferon on human HT29m colon carcinoma cells and human kidney carcinoma cells Sn12CL1 growing in tissue culture. The synergistic effects of swainsonine and $\alpha_2$-interferon on human carcinoma cell growth are similar to that observed for the murine lymphoreticular tumor cell line.

DESCRIPTION OF THE DRAWINGS

Further details of the invention are described below with the help of the examples illustrated in the accompanying drawings in which.

DETAILED DESCRIPTION

Figure 1:
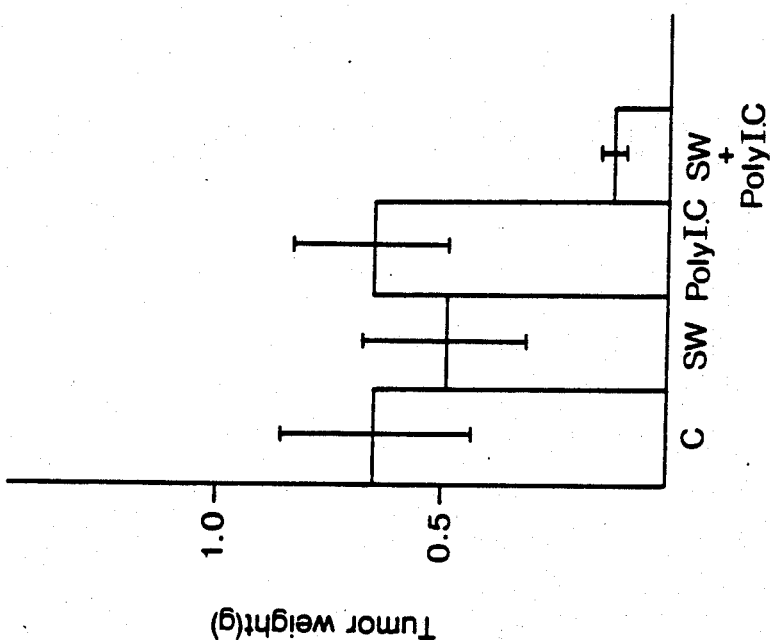
FIG. 1 is a graph showing the growth of MDAY-D2 tumors in mice given one or both of swainsonine (SW)-supplemented drinking water and two i.p. injections of poly (I.C.)

The invention relates to a composition comprising an inhibitor of Golgi α-mannosidase II and which may contain an interferon or interferon inducer. The composition comprising an inhibitor of Golgi α-mannosidase II, in pharmaceutical formulation inhibits cancer metastasis and cell proliferation. The enhancing composition comprising an inhibitor of Golgi α-mannosidase II and interferon or interferon inducer enhances the antiproliferative and antiviral effects of interferon or interferon inducers and inhibits neoplastic growth and metastasis.

Suitable inhibitors of Golgi α-mannosidase II are swainsonine and active analogues of swainsonine.

Suitable interferons and interferon inducers for the enhancing composition of the invention are α-interferons, β-interferons, γ-interferons, poly (I.C.), poly (I.C.) complexed with poly L-lysine (poly (I.C.)-LC), tumor necrosis factor (TNF), transforming growth factor (TGF), preferably α-interferons and β-interferons. acceptable carrier such as, for example, fillers, emulsifiers, lubricants, or buffer substances. The components are brought using customary methods into a suitable formulation form such as, for example, tablets or capsules for oral administration or a suspension or solution suitable for oral, intravenous, intramuscular or intraperitoneal administration.

The administration of the inhibitor of Golgi α-mannosidase II and pharmaceutcially acceptable carrier effects a reduction in metastasis and cell proliferation and thus may be used for the treatment of various forms of cancer. More specifically, such compositions may be used for treating various forms of neoplasia, such as leukemias, lymphomas, sarcomas, melanomas, adenomas, carcinomas of solid tissues and benign lesions such as papillomas. The composition may be used to treat humans and various other mammals.

Preferred enhancing compositions according to the invention are those which contain swainsonine and α-, β- or γ-interferon or poly (I.C.) or poly (I.C.)-LC, or TNF, or TGF, preferably α- or β-interferon.

The combination of the α-mannosidase II inhibitor and interferon or interferon inducer effects an enhanced antiproliferative effect and inhibits neoplastic growth and metastasis and thus may be used for various types of therapy, for example, in treatment of various forms of cancer. The enhancing compositions according to the invention may be especially beneficial when the therapies are used following chemotherapy or radiotherapy. More specifically, the enhancing compositions may be used for treating various forms of neoplasia, such as leukemias, lymphomas, melanomas, adenomas, sarcomas, carcinomas of solid tissues, tumors of the nervous system and benign lesions such as papillomas. The enhancing composition may be used for other proliferative conditions such as arthrosclerosis and viral infections. The enhancing composition may be used to treat humans and various other mammals.

The concentrations of the components of the compositions of the invention vary depending on the activity of the components. For the inhibitor, the concentration is between 0.03–300 μg/g. For the interferon or interferon inducer, the concentration, for example, of poly (I.C.) and poly (I.C.)-LC, is between 0.1 mg–100 mg/m² and for α- or β-interferon the concentration is between $10^2$–$5 \times 10^7$ units/m².

The invention also relates to a method for the prevention and treatment of cancer metastasis and cell proliferation comprising administering to a patient an effective amount of an inhibitor of Golgi α-mannosidase II and a pharmaceutically acceptable carrier.

The invention further relates to a method for the prevention and treatment of proliferative disorders, viral infections, and neoplastic growth, and metastasis, comprising administering to a patient an effective amount of an inhibitor of the Golgi enzyme α-mannosidase II and an effective amount of an interferon or interferon inducer.

The inhibitor and interferon or interferon inducer may be administered concurrently, separately or sequentially. For swainsonine and α- or β-interferon, for example, the swainsonine may be administered one or more times daily with one injection of α- or β-interferon daily.

The inhibitor in appropriate pharmaceutical formulation may be administered orally, intravenously intraperitoneally, preferably orally. For a form for oral administration, the inhibitor is converted by customary methods into suitable forms for administration, such as aqueous solutions, tablets, and capsules. For intravenous, intramuscular or intraperitoneal administration the inhibitor and a pharmaceutically acceptable carrier are brought using customary methods, into a solution, suspension or emulsion.

The interferon or interferon inducer in appropriate pharmaceutical formulation, may be administered intravenously, intramuscularly or intraperitoneally, or locally at the tumor. For intravenous, intramuscular, intraperitoneal, or local administration, the inferferon or interferon inducer is converted into a solution, suspension or emulsion, where desired with the substances customary for this purpose, such as solubilizers, emulsifiers or other auxiliaries. Examples of suitable solvents are water, physiological saline solutions, albumin, carboxymethylceullose solutions, and protein stabilizers.

In accordance with the method of the invention for prevention and treatment of cancer metastasis and cell proliferation comprising administering to a patient an effective amount of an inhibitor of the Golgi enzyme α-mannosidase II and a pharmaceutically acceptable carrier, the sufficient doses of the inhibitor is that which is approximately the minimum dose adequate to reduce metastasis and/or shown an antiproliferative effect. The doses will also depend on the body weight and constitution of the patient.

In accordance with the method of the invention for prevention and treatment of proliferative disorders, viral infections and neoplastic growth, and metastasis, comprising administering to a patient an effective amount of an inhibitor of the Golgi enzyme α-mannosidase II and an effective amount of an interferon or interferon inducer, the doses of the inhibitor and interferon or interferon inducer are each selected so that the inhibitor and interferon or interferon inducer alone would not show a full effect. The sufficient doses of the inhibitor and interferon or interferon inducers are those which are approximately the minimum doses adequate for enhanced antiproliferative or antiviral effects or inhibition of neoplastic growth and metastasis. The doses of the components will also depend on the body weight and constitution of the patient.

For the methods according to the invention in humans and other mammals, for example, the doses of the inhibitors range from 0.03–300 μg/g body weight, preferably 1–10 μg/ body weight. The doses of poly (I.C.) and poly (I.C.)-LC range from 0.01–100 mg/m² and those of α- or β-interferon range from $10^2-5\times10^7$ units/m².

The following non-limiting examples are illustrative of the present invention:

EXAMPLE 1

Lung Colonization by B16F10 PMelanoma Cells

B16F10 tumor cells were cultured for 48 hours in the presence or absence of swainsonine (0.3 μg/ml) before injection of $10^5$ cells into the lateral tail veins of C57BL mice on day 0. Mice were given drinking water with 2.5 μg/ml swainsonine 2 days before tumor cells were injected and maintained on swainsonine for 17 days. Mice injected with poly (I.C.) were given an intraperitoneal injection of 100 μg the day before tumor cells.

Lung nodules were counted on day 24 and each group consisted of 5 mice.

The results in Table 1 show that the addition of swainsonine at 2.5 μg/ml to the drinking water of the C57BL mice reduced organ colonization by B16F10 melanoma cells.

TABLE 1

Lung Colonization by murine B16F10 melanoma cells

| Treatment[a] | | Lung Nodules[b] | | |
|---|---|---|---|---|
| cells | mice | Exp 1 | (mean +/− S.D.) | Exp 2 |
| Nil | Nil | 58 ± 33 | | >100 |
| Nil | poly I.C. | 37 ± 40 | N.S. | N.D. |
| SW | Nil | 16 ± 12 | (p < .02) | 44 ± 36 |
| SW | poly I.C. | 24 ± 18 | (p < .05) | 2 ± 2 |
| SW | SW | 5 ± 6 | (p < .005) | N.D. |
| SW | SW + poly I.C. | 4 ± 4 | (p < .005) | 0 ± 0 |

N.D. and N.S. refer to not done and no statistical difference, respectively.

EXAMPLE 2

Experimental Metastasis of Murine MDAY-D2 Tumor Cells

MDAY-D2 tumor cells were cultured for 48 hours in the presence or absence of swainsonine (0.3 μg/ml) before injecting $10^4$ cells into the lateral tail veins of mice on day 0. Mice were given drinking water with swainsonine (2.5 μg/ml) 2 days before tumor cells were injected and maintained on the swainsonine for 17 days. Mice injected with poly (I.C.) were given an intraperitoneal injection of 100 μg the day before tumor cells were injected and again on day 3. Those that survived longer than 100 days were tumor free and scored as long-term survivors.

Mice given injections of swainsonine-treated cells (Table 2) showed a signficantly higher frequency of long-term survivors compared to those given injections of untreated cells. A higher frequency of long-term survivors was also observed in mice administered swainsonine.

TABLE 2

Experimental metastasis of MDAY-D2 tumor cells

| Treatment | | Long-term survivors/no. of mice given injections | |
|---|---|---|---|
| Cells | Mice | Experiment 1 | Experiment 2 |
| Nil | Nil | 0/5 | 0/5 |
| Nil | Poly (I.C.) | 0/5 | 0/5 |
| Swainsonine | Nil | 3/5 | 1/5 |
| Swainsonine | Poly (I.C.) | 2/5 | 0/5 |
| Swainsonine | Swainsonine | Not done | 1/5 |
| Swainsonine | Swainsonine + poly (I.C.) | Not done | 3/5 |

EXAMPLE 3

Swainsonine and Poly (I.C.)-inhibited Solid Tumor Growth

Mice were provided with drinking water with swainsonine (2.5 μg/ml) 2 days before $10^5$ MDAY-D2 tumor cells were injected. Poly (I.C.) was injected i.p. 1 day before and 2 days after tumor cells were injected. Tumors were removed on day 15 and weighed. The growth of MDAY-D2 tumors in mice given swainsonine supplemented drinking water and/or two i.p. injections of poly (I.C.) are shown in FIG. 1. The combination of the swainsonine added to the drinking water and two i.p. injections of poly (I.C.) reduced the rate of growth of the MDAY-D2 tumors. Poly I.C. and swainsonine synergized to inhibit MDAY-D2 tumor growth in situ.

EXAMPLE 4

Enhancement of the Antiproliferative effect of Interferon by Swainsonine

Figure 2:
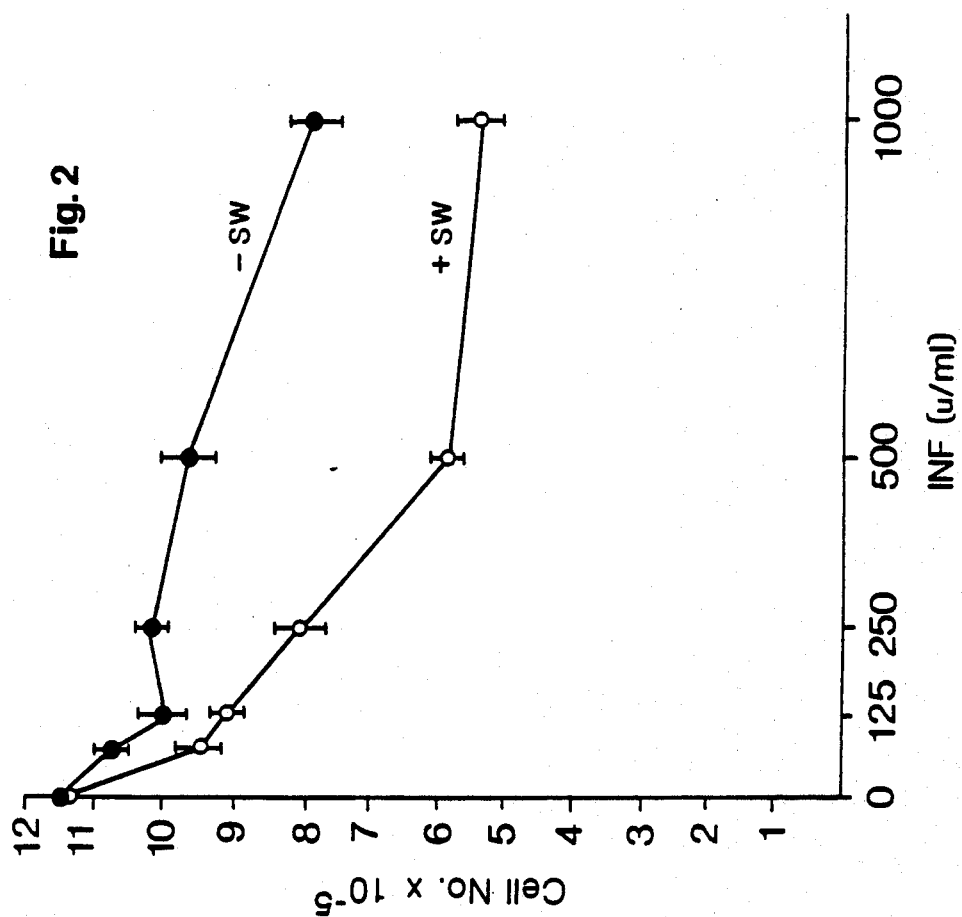
FIG. 2 is a graph showing the enhancement of the antiproliferative effect of interferon by swainsonine is tissue culture.

MDAY-D2 tumor cells were seeded into tissue culture plates at $10^3$/ml and serial dilutions of mouse α/β-interferon (Sigma) were added. The cells were cultured in the presence and absence of swainsonine (1 μg/ml) and on day 5 the cell number was determined using a Coulter Counter. The results in FIG. 2 show that swainsonine enhanced the antiproliferative effect of α/β-interferon.

EXAMPLE 5

Effect of Swainsonine and Poly (I.C.) on the Survivial of Mice Bearing Established MDAY-D2 metastasis MDAY-D2 tumor cells were injected S.C. and the resulting tumors were surgically resected 12 days later. The mice were divided into 4 treatment groups. Poly (I.C.) was administered on days 12 and 15, and swainsonine-supplemented drinking water was provided between days 12 and 30. The survival time was determined up to 90 days and mice surviving more than 90 days were considered long-term survivors.

Figure 3:
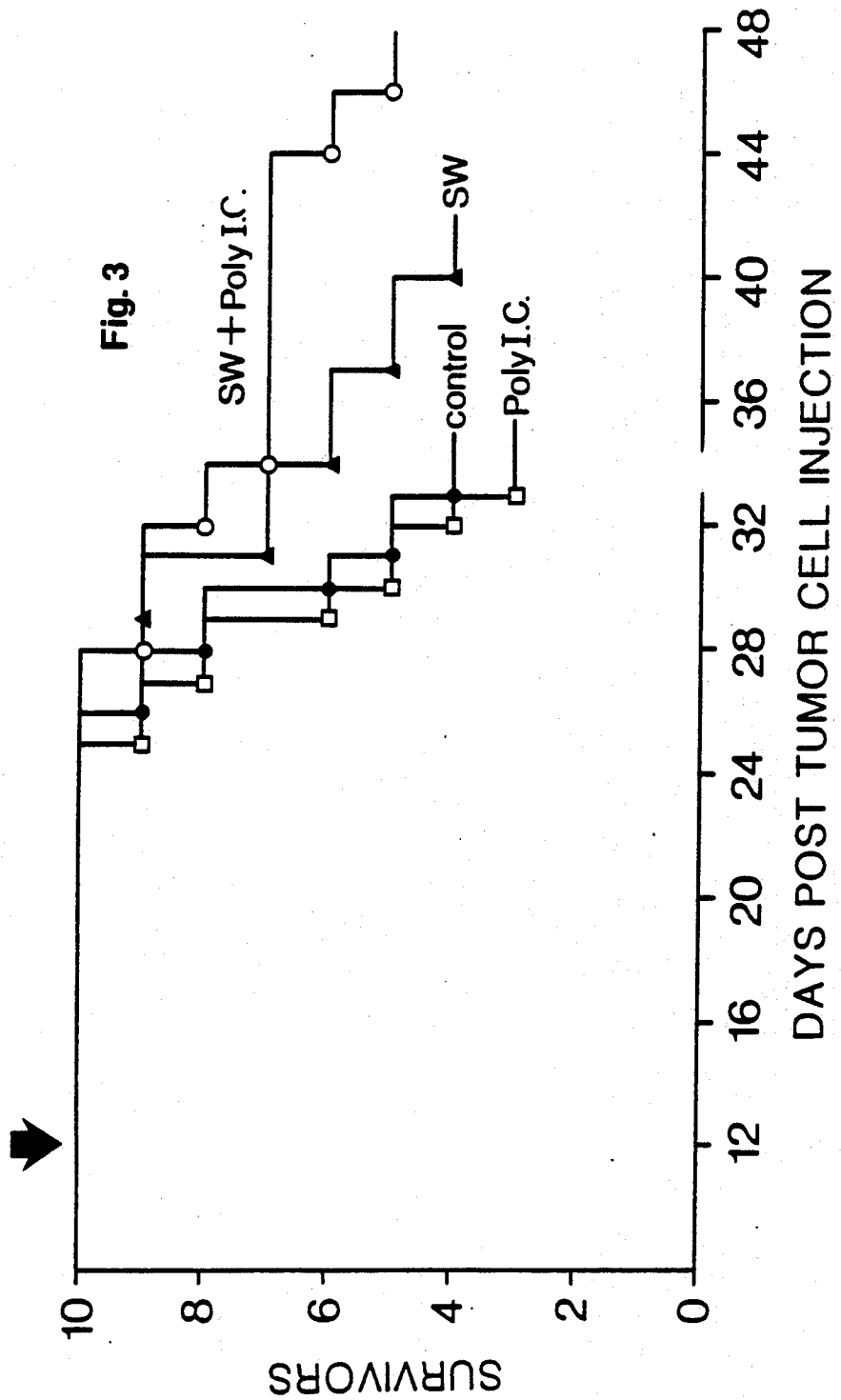
FIG. 3 is a graph showing the effect of swainsonine and poly (I.C.) on the survival of mice bearing established MDAY-D2 metastases.

FIG. 3 shows the effect of swainsonine and poly (I.C.) on the survival of mice bearing established MDAY-D2 metastasis. The combination of swainsonine and poly (I.C.) increased the survival time of the mice.

EXAMPLE 6

Human colon carcinoma (HT29m) were cultured for 48 hours in the presence or absence of swainsonine (1 μg/ml) before injecting $10^6$ cells intravenously into mice. The results in Table 3 show that swainsonine reduced metastasis of human colon carcinoma cells (HT29m).

TABLE 3

Experimental Metastasis of Human Colon Carcinoma Cells (HT29m) in Nude Mice

| Treatment of HT29M | Mice with Metastasis | Mean No. of Lesions/Mouse |
|---|---|---|
| Nil | 4/5 | 2.4 |
| SW | 2/5 | 0.6 |

EXAMPLE 7

Human colon carcinoma cells (HT29m) and human kidney carcinoma cells (SN12CL1) were grown in medium containing 7% fetal calf serum with no additions (C); 1 μg/ml of swainsonine (SW); 1000 units of human α2-interferon (α2); or a combination of swainsonine and α2-interferon (SW++α2). The cells were plated on day 1 at $10^5$/ml and counted 4 days later. Cells in swainsonine were pre-grown in swainsonine for 48 hours before setting up the experiment on day 0.

Figure 4:
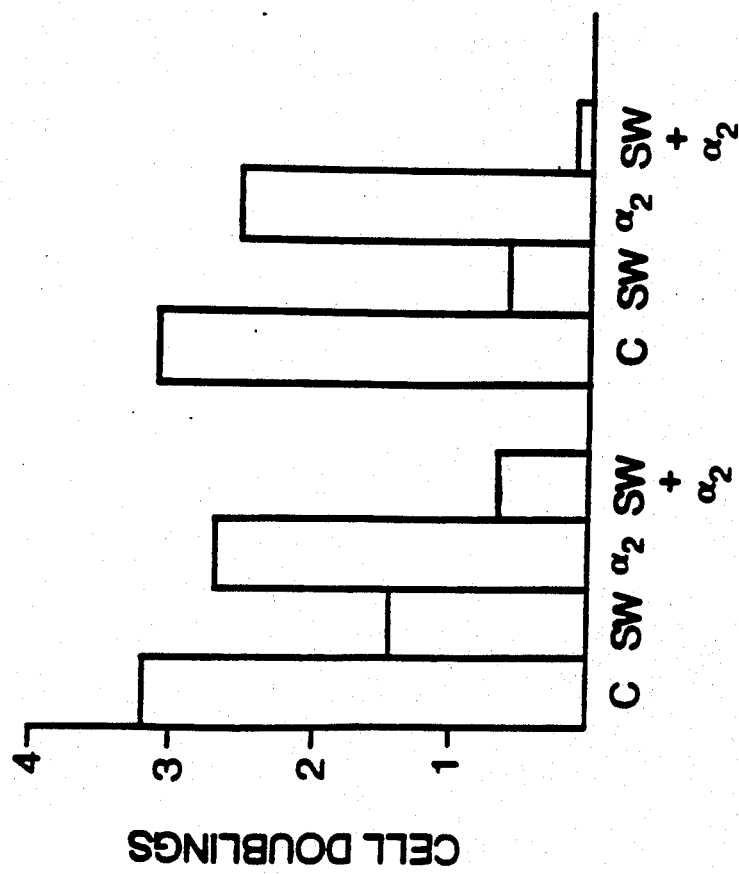
FIG. 4 is a bar graph showing the antiproliferative effect of $\alpha_2$-interferon and/or swainsonine in tissue culture using human HT29m color carcinoma and SN12LC1 renal carcinoma cells.

The results in FIG. 4 show that swainsonine alone reduced the proliferation of human carcinoma cells growing in tissue culture. Swainsonine also enhanced the antiproliferative effects of human α2-interferon on human carcinoma cells growing in tissue culture. The antiproliferative effects demonstrated here parallel those observed for the tumor cells growing in nude mice described in examples 8 and 9.

EXAMPLE 8

Balb/c nude mice were injected subcutaneously with $10^5$ human colon carcinoma cells (HT29m) and tumor growth was monitored. Mice were grouped into treatment groups that received 2.5 μg/ml of swainsonine in their drinking water (SW); $10^4$ units of human α2-interferon administered intravenously twice a week (α2); both 2.5 μg/ml of swainsonine in the drinking water and $10^4$ units of human α2-interferon administered intravenously twice a week (SW+α2); or none of the treatments (nil). Treatment began at day 1 and was continued until the mice were sacrificed on day 47.

Figure 5:
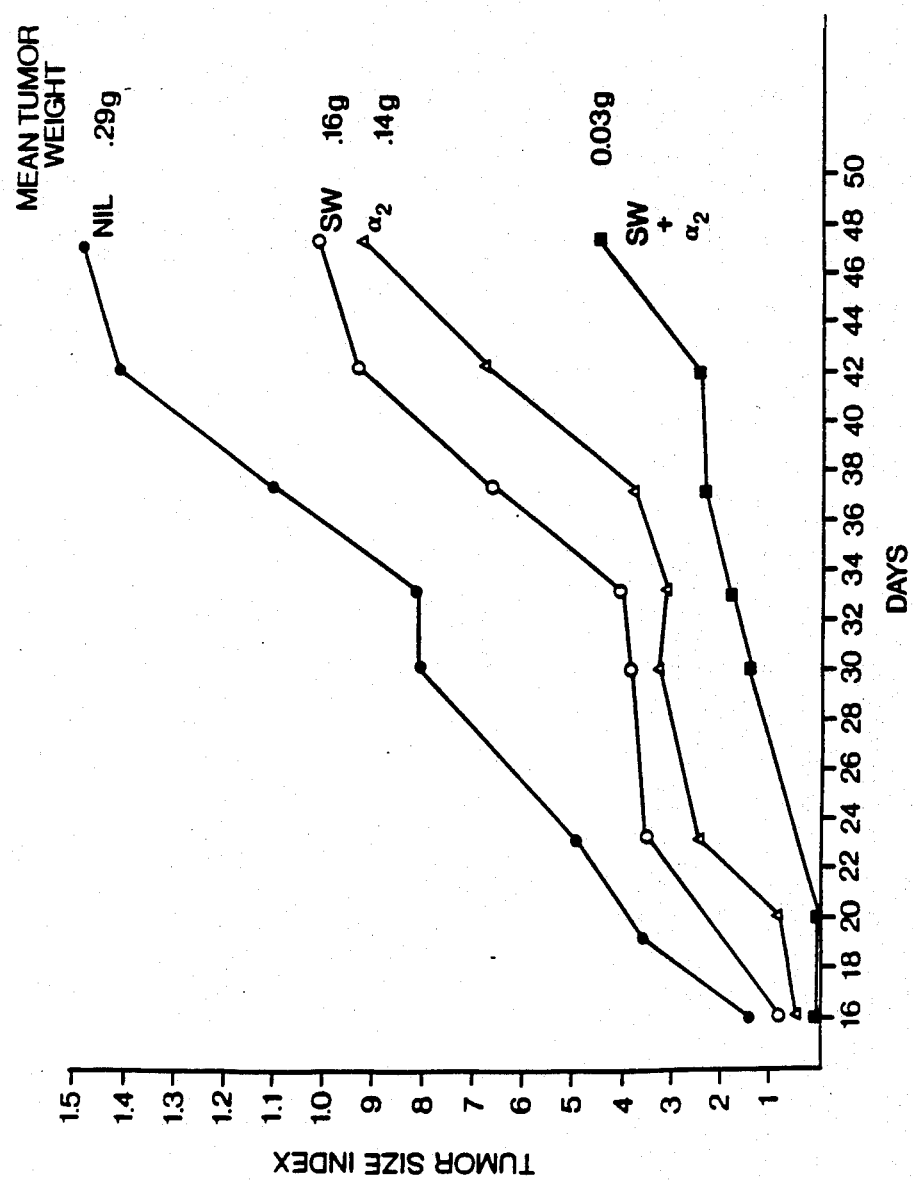
FIG. 5 is a graph showing the growth of human HT29m colon carcinoma cells in nude mice treated with one or both of SW-supplemented drinking water and two i.v. injections of human $\alpha_2$-interferon per week.

The results in FIG. 5 show that swainsonine alone reduced the growth rate of human carcinoma cells transplanted into nude mice. Swainsonine in combination with human α2-interferon synergized to inhibit human carcinoma cell growth in nude mice.

EXAMPLE 9

Balb/c nude mice were injected subcutaneously with $10^5$ human colon carcinoma cells (HT29m) and tumor growth was monitored. Mice were grouped into treatment groups that received 2.5 μg/ml of swainsonine in their drinking water (SW); 100 μg/ml of poly I.C. administered intraperatoneally twice a week (POLY I.C.); 2.5 μg/ml of swainsonine in their drinking water and 100 μg of poly I.C. administered intraperitoneally twice a week (SW+POLY I.C.); or, none of the treatments (nil). Treatment began at day 1 and was continued until the mice were sacrificed on day 39.

Figure 6:
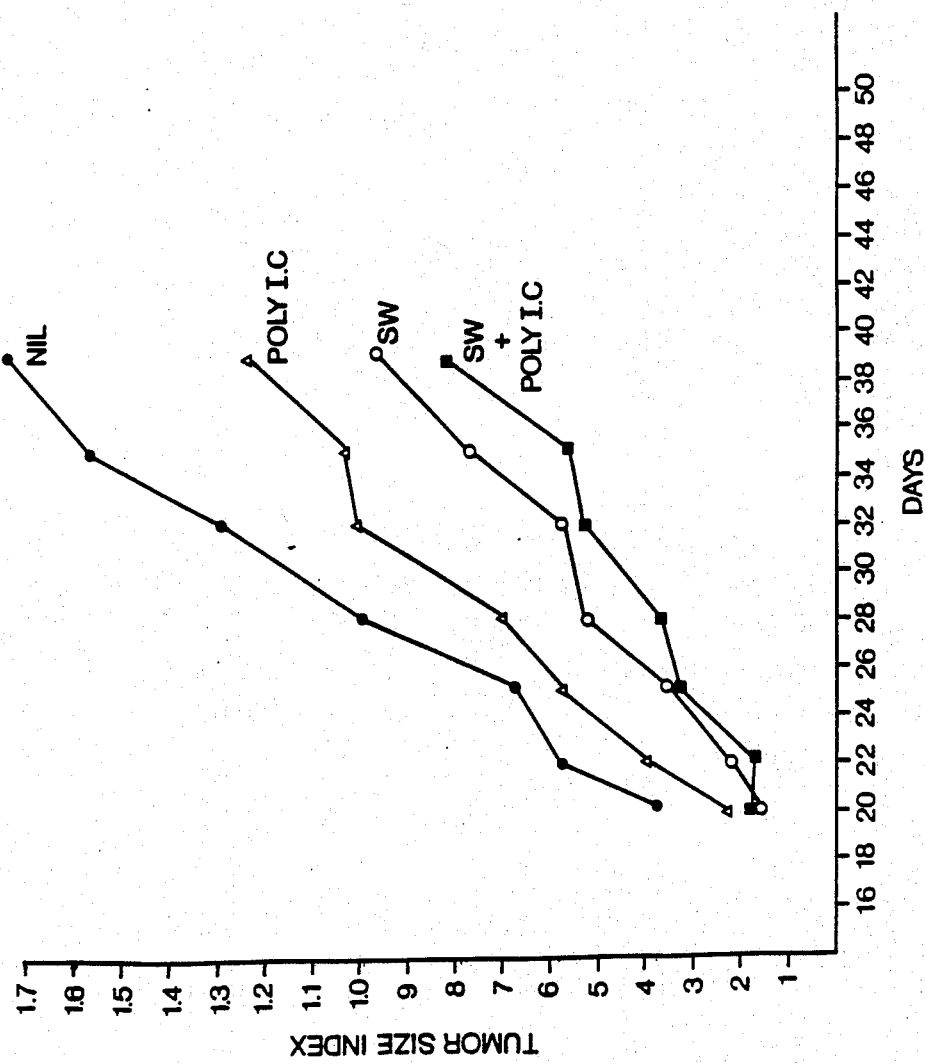
FIG. 6 is a graph showing the growth of human HT29m colon carcinoma cells in nude mice treated with one or both of SW-supplemented drinking water and two i.v. injection of poly I.C. per week; and, FIG. 7 is an autoradigram of a Northern blot probed for c-myc to compare the levels of c-myc mRNA in untreated (A), swainsonine treated (B), interferon treated (C), HT29m cells.

The results in FIG. 6 show that swainsonine alone reduced the growth rate of human carcinoma cells transplanted into nude mice. Swainsonine in combination with poly I.C. synergized to inhibit human carcinoma cell growth in nude mice. The synergistic effect observed was not of the same magnitude as observed with respect to example 8. This is probably due to the non-cross reactive nature of mouse and human interferons. The administration of poly I.C. induces mouse interferon in situ which would not be active on the human carcinoma cells.

EXAMPLE 10

Total RNA was extracted from RT29m human colon carcinoma cells grown in the presence or absence of 1 μg/ml of swainsonine for 48 hours or 1000 units/ml of interferon A/D. Total RNA (10 μg) was electrophoretically separated and transfected to nitrocellulose. c-myc mRNA transcripts were deleted in a standard Northern blotting procedure using an exon II fragment of mouse c-myc derived from MOPC 315 mouse plasmacytoma carried in the vector pSV-c-myc-1.

Figure 7:
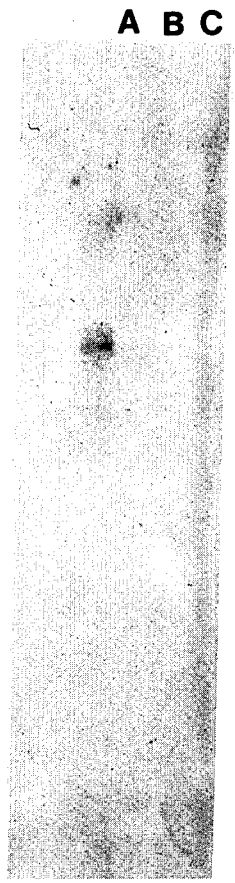

HT29 human colon carcinoma cells cultured in the presence of swainsonine (B) showed decreased c-myc expression. (FIG. 7).

I claim:
1. A composition which enhances the antiproliferative and antiviral effects of interferons or interferon inducers, and inhibits neoplastic growth and metastasis, comprising an effective amount of swainsonine or an active analogue of swainsonine and an effective amount of an interferon or interferon inducer.

2. A composition as claimed in claim 1, wherein the interferon is α- or β-interferon.

3. A composition as claimed in claim 1, wherein the interferon inducer is poly (I.C.).

4. A composition as claimed in claim 1, 2 or 3, wherein the concentration of swainsonine is between 0.03–300 mg/kg body weight.

5. A composition as claimed in claim 2, wherein the concentration of α- or β-interferon is between $10^2$–$5 \times 10^7$ units/m² of body surface.

6. A method for the treatment of proliferative disorders, viral infections and neoplastic growth and metastasis, comprising administering to a patient an effective amount of swainsonine or an active analogue of swainsonine and an effective amount of an interferon or interferon inducer.

7. A method as claimed in claim 6, wherein the interferon is α or β-interferon.

8. A method as claimed in claim 6, wherein the interferon inducer is poly (I.C.).

9. A method as claimed in claim 7 or 8, wherein the amount of swainsonine administered is between 0.03–300 mg/kg body weight.

10. A method as claimed in claim 7, wherein the amount of α- or β-interferon administered is between $10^2$–$5 \times 10^7$ units/m² of body surface.

11. A method as claimed in claim 8, wherein the amount of poly (I.C.) administered is between 0.01–100 mg/m² of body surface.

12. A method as claimed in claim 6, wherein the swainsonine on an active analgue of swainsonine is administered orally and the interferon or interferon inducer is administered intravenously, intramuscularly, intraperitoneally, or locally.

13. A method as claimed in claim 7, wherein the swainsonine is administered orally, and the α- or β-interferon is administered intravenously.

14. A method as claimed in claim 8, wherein the swainsonine is administered orally and the poly (I.C.) is administered intravenously.

15. A composition which inhibits growth and metastasis of a neoplasia, comprising an effective amount of swainsonine or an active analogue of swainsonine and an effective amount of an interferon or interferon inducer.

16. A composition as claimed in claim 15, wherein the neoplasia is a tumor of the lymphoreticular system, a melanoma, or a carcinoma of solid tissue.

17. A method for the treatment of growth and metastasis of a neoplasia, comprising administering to a patient an effective amount of swainsonine and an effective amount of an interferon or interferon inducer.

18. A method as claimed in claim 17, wherein the neoplasia is a tumor of the lymphoreticular system, a melanoma, or a carcinoma of solid tissue.

* * * * *